United States Patent
Lauman et al.

(10) Patent No.: US 7,458,951 B2
(45) Date of Patent: Dec. 2, 2008

(54) METHOD OF STRUCTURING A MACHINE TO HEAT DIALYSIS FLUID USING RADIANT ENERGY

(75) Inventors: Brian Lauman, Clearwater, FL (US); John Parish, Clearwater, FL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 11/616,204

(22) Filed: Dec. 26, 2006

(65) Prior Publication Data

US 2007/0106197 A1    May 10, 2007

Related U.S. Application Data

(62) Division of application No. 10/051,609, filed on Jan. 17, 2002, now Pat. No. 7,153,285.

(51) Int. Cl.
*A61M 37/00* (2006.01)
*A61F 7/00* (2006.01)

(52) U.S. Cl. ............... 604/6.08; 604/113; 604/114

(58) Field of Classification Search ............ 604/6.08, 604/28–29, 113–114; 607/104–106
See application file for complete search history.

(56) References Cited

U.S. PATENT DOCUMENTS

| | | | |
|---|---|---|---|
| 3,475,590 A | 10/1969 | Pins | |
| 3,485,245 A | 12/1969 | Lahr et al. | |
| 4,180,460 A | 12/1979 | Calari | |
| 4,191,646 A | 3/1980 | Larsson et al. | |
| 4,194,536 A | 3/1980 | Stine et al. | |
| 4,276,175 A | 6/1981 | Bower | |
| 4,293,762 A * | 10/1981 | Ogawa | 392/470 |
| 4,309,592 A | 1/1982 | Le Beouf | |
| 4,396,382 A | 8/1983 | Goldhaber | |
| 4,412,917 A | 11/1983 | Ahjopalo | |
| 4,464,563 A | 8/1984 | Jewett | |
| 4,488,961 A | 12/1984 | Spencer | |
| 4,532,414 A | 7/1985 | Shah et al. | |
| RE32,303 E | 12/1986 | Lasker et al. | |
| 4,655,753 A | 4/1987 | Bellotti et al. | |

(Continued)

FOREIGN PATENT DOCUMENTS

DE    26 44 937 A1    4/1978

(Continued)

OTHER PUBLICATIONS

Office Action mailed Aug. 14, 2008, for corresponding Japanese Pat. Appl. 2003-561680, citing above Japanese Laid-Open Publication 10-024102 (English translation only).

*Primary Examiner*—Kevin C. Simons
*Assistant Examiner*—Andrew M Gilbert
(74) *Attorney, Agent, or Firm*—Joseph P. Reagen; Bell, Boyd & Lloyd LLC

(57) ABSTRACT

A method of structuring a machine to heat a dialysis fluid includes: (i) allowing flow of the dialysis fluid through a disposable fluid conduit; (ii) directing energy from a 2-dimensional energy source to apply energy to the dialysis fluid in the disposable fluid conduit; and (iii) directing energy from a 3-dimensional energy source to apply energy to the dialysis fluid in the disposable fluid conduit.

8 Claims, 6 Drawing Sheets

U.S. PATENT DOCUMENTS

| | | | |
|---|---|---|---|
| 4,678,460 A | 7/1987 | Rosner | |
| 4,680,445 A | 7/1987 | Ogawa | |
| 4,728,496 A | 3/1988 | Petersen et al. | |
| 4,735,609 A | 4/1988 | Comeau et al. | |
| 4,769,151 A | 9/1988 | Shouldice | |
| 4,844,074 A | 7/1989 | Kurucz | |
| 4,847,470 A | 7/1989 | Bakke | |
| 4,906,816 A * | 3/1990 | van Leerdam | 392/470 |
| 5,073,167 A | 12/1991 | Carr et al. | |
| 5,125,069 A | 6/1992 | O'Boyle | |
| 5,180,896 A | 1/1993 | Gibby et al. | |
| 5,245,693 A | 9/1993 | Ford et al. | |
| 5,271,086 A * | 12/1993 | Kamiyama et al. | 392/483 |
| 5,370,674 A | 12/1994 | Farrell | |
| 5,381,510 A | 1/1995 | Ford et al. | |
| 5,382,805 A | 1/1995 | Fannon et al. | |
| 5,408,576 A | 4/1995 | Bishop | |
| 5,420,962 A | 5/1995 | Bakke | |
| 5,474,683 A | 12/1995 | Bryant et al. | |
| 5,542,919 A | 8/1996 | Simon et al. | |
| 5,559,924 A * | 9/1996 | Kadotani et al. | 392/483 |
| 5,641,405 A | 6/1997 | Keshaviah et al. | |
| 5,683,381 A | 11/1997 | Carr et al. | |
| 5,690,614 A | 11/1997 | Carr et al. | |
| 5,724,478 A | 3/1998 | Thweatt | |
| 5,729,653 A | 3/1998 | Magliochetti et al. | |
| 5,740,315 A | 4/1998 | Onishi et al. | |
| 5,790,752 A | 8/1998 | Anglin et al. | |
| 5,836,908 A | 11/1998 | Beden et al. | |
| 5,875,282 A | 2/1999 | Jordan et al. | |
| 5,925,011 A | 7/1999 | Faict et al. | |
| 5,938,634 A | 8/1999 | Packard | |
| 5,960,160 A | 9/1999 | Clark et al. | |
| 5,989,238 A | 11/1999 | Ginsburg | |
| 6,069,343 A | 5/2000 | Kolowich | |
| 6,139,528 A | 10/2000 | Kistner et al. | |
| 6,142,974 A | 11/2000 | Kistner et al. | |
| 6,146,359 A | 11/2000 | Carr et al. | |
| 6,175,688 B1 | 1/2001 | Cassidy et al. | |
| 6,205,292 B1 * | 3/2001 | Pokorny et al. | 392/489 |
| 6,228,047 B1 | 5/2001 | Dadson | |
| 6,229,957 B1 | 5/2001 | Baker | |
| 6,236,809 B1 | 5/2001 | Cassidy et al. | |
| 6,257,265 B1 | 7/2001 | Brunner et al. | |
| 6,259,074 B1 | 7/2001 | Brunner et al. | |
| 6,261,261 B1 * | 7/2001 | Gordon | 604/113 |
| 6,869,538 B2 * | 3/2005 | Yu et al. | 210/742 |
| 7,153,286 B2 * | 12/2006 | Busby et al. | 604/6.11 |
| 2002/0096984 A1 | 7/2002 | Konishi et al. | |
| 2003/0004470 A1 | 1/2003 | Hickerson et al. | |

FOREIGN PATENT DOCUMENTS

| | | |
|---|---|---|
| DE | 28 33 730 A1 | 2/1980 |
| DE | 198 14 695 A1 | 10/1999 |
| DE | 198 28 923 A1 | 5/2000 |
| EP | 0 570 586 A1 | 11/1993 |
| EP | 0 575 512 B1 | 12/1993 |
| EP | 0 956 876 A1 | 11/1999 |
| GB | 2242367 | 10/1991 |
| JP | 6-106033 | 4/1994 |
| JP | 10024102 | 1/1998 |
| WO | WO 00/57928 | 10/2000 |

* cited by examiner

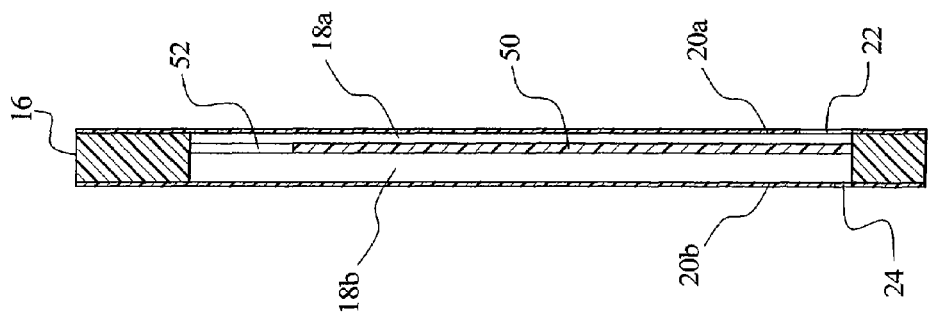
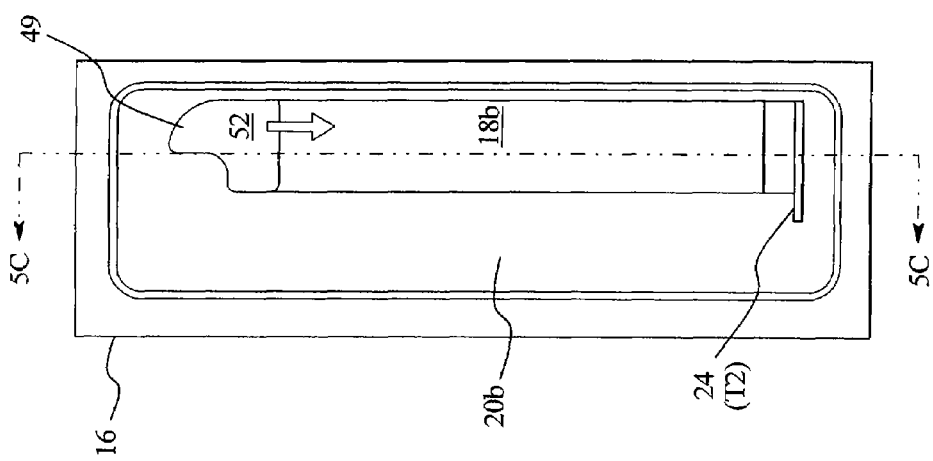
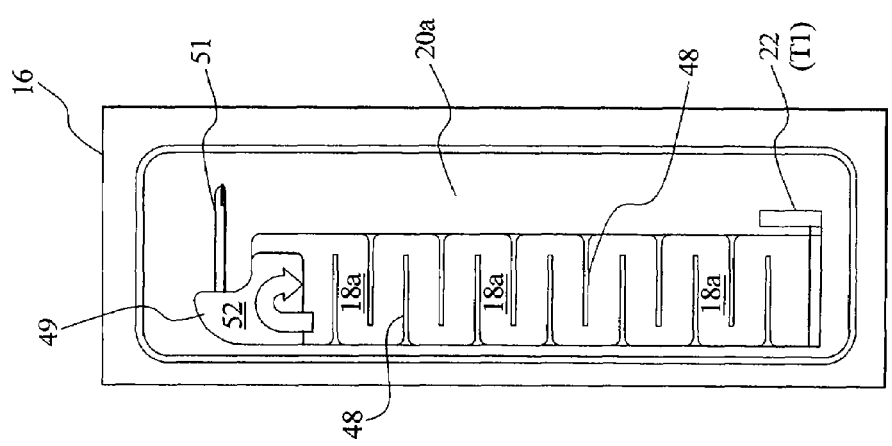

METHOD OF STRUCTURING A MACHINE TO HEAT DIALYSIS FLUID USING RADIANT ENERGY

PRIORITY

This application claims priority to and the benefit as a divisional application of U.S. Ser. No. 10/051,609 U.S. Pat. No. 7,153,285 "Medical Fluid Heater Using Radiant Energy", filed Jan. 17, 2002, the disclosure of which is incorporated herein by reference.

BACKGROUND

The present disclosure generally relates to fluid heaters. More specifically, the present disclosure relates to parenteral fluid heaters and methods of heating parenteral fluids. In an embodiment, the present disclosure relates to fluid heaters for use in dialysis systems.

Due to disease, insult or other causes, a person's renal system can fail. In renal failure of any cause, there are several physiological derangements. The balance of water, minerals and the excretion of daily metabolic load is no longer possible in renal failure. During renal failure, toxic end products of nitrogen metabolism (urea, creatinine, uric acid, and others) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys. Hemodialysis and peritoneal dialysis are two types of dialysis therapies commonly used to treat loss of kidney function.

Peritoneal dialysis utilizes a dialysis solution or dialysate, which is infused into a patient's peritoneal cavity. The dialysate contacts the patient's peritoneal membrane in the peritoneal cavity. Waste, toxins, and excess water pass from the patient's bloodstream through the peritoneal membrane and into the dialysate. The transfer of waste, toxins, and water from the bloodstream into the dialysate occurs by diffusion and osmosis because there is an osmotic gradient across the peritoneal membrane. The spent dialysate is drained from the patient's peritoneal cavity to remove the waste, toxins, and water from the patient and then replaced.

Prior to infusion into the peritoneal cavity, the dialysis solution is frequently at a temperature lower than body temperature. For example, the dialysis solution may be at room temperature or even colder. Dialysis solution can be particularly cold when stored in a cold place or exposed to cold weather. Using dialysate that is cold relative to the patient undesirably cools the patient and can cause the patient discomfort during the dialysis procedure. Accordingly, it is desirable to heat the dialysate to about body temperature prior to infusion into the patient's peritoneal cavity.

Hemodialysis treatment utilizes the patient's blood to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. It is also desirable to heat fluids, for example blood and dialysate, used in hemodialysis to about body temperature.

Heating dialysis fluids to temperatures comfortable to the patient has historically been accomplished using electrical resistive plate heaters. Resistive plate heaters increase in temperature when electricity is applied to the resistive plate. The resistive plate heaters are in direct contact with a fluid container and transfer heat from the plate to the fluid in the container.

Two types of existing resistive plate heaters include a bulk plate heater and an in-line plate heater. A bulk plate heater can have a relatively large dialysate container, such as a two liter dialysate reservoir bag, placed on top of the heater plate. The bulk plate heater heats the fluid close to the heater plate in the reservoir bag, and over time the temperature increase spreads throughout the fluid in the bag to heat all of the dialysate fluid. In-line plate heaters heat dialysate fluid as the fluid flows through a relatively smaller bag in contact with the heater plate. In-line plate heaters purport to heat fluid on demand as the fluid flows past the heater plate, whereas bulk plate heaters provide a reservoir of heated fluid.

Resistive plate heaters have also been used for heating fluids during hemodialysis and intravenous administration of fluids. Although resistive plate heaters have been used to heat fluids for dialysis treatments and other applications, resistive plate heaters have limitations. For example, the heating capacity of a plate heater is dependant on the surface area of the heater plate. If larger dialysate loads need to be heated, the size of the surface area of the heater plate must be increased. Increasing the size of the heater may not be desired for various reasons, such as requiring more space or higher electrical power consumption. Alternatively, the temperature of the heater plate can be increased; however, higher temperatures may not be desired. For example, the temperature of the heater plate may be limited to safe levels for the fluid being heated or to safe levels for the fluid container in contact with the heater plate.

Another limitation with resistive plate heaters is that the heaters are two-dimensional, i.e., the heaters transfer heat energy over the two-dimensional surface area of the heater plate. Temperature increase of the fluid being heated occurs at the interface between the fluid and the fluid container, i.e, sheeting which contacts the heater plate. Accordingly, the plate heater only directly heats one surface of the fluid. The remaining fluid is heated by heat conduction and convection from the heated surface. The two-dimensional heating of the dialysate fluid limits the depth of a dialysate container in a bulk heating operation and the fluid flow rate in an in-line operation. Further, the wall of the dialysate container in either type of operation necessarily lowers the heating response time of the system in comparison to a direct contact of the fluid with a heat source. A flexible plastic dialysate bag material typically does not have good thermal conductivity. Known bulk and in-line heaters can consequently have a slow response time when a relatively large dialysate load needs to be heated.

Another problem with known bulk and in-line heaters is that the dialysate bag or container, which is a necessary component in either system, gives off heat as the bulk or in-line heat plate attempts to heat the dialysate fluid. The heat plate heats one side of the container, while the remaining sides of the container give off heat to the atmosphere due to convective or evaporative cooling.

A further problem with the present bulk and in-line dialysate heaters is that the heat plates remain hot for a period of time after being turned off. That is, the stored thermal energy of the heated plates does not immediately dissipate when the electricity powering the plates is cut off. The result is that either the system throws away the additional heat or shuts down the heater prior to the time that the fluid reaches its desired temperature in an attempt to use the residual heat to heat the fluid to its desired temperature. The first option creates inefficiency, while the second option increases complexity and chance for error. Generally, accurate control of the fluid temperature is difficult with bulk fluid heaters.

Accordingly, a need exists to provide a more efficient dialysate heater, which is capable of heating relatively large dialysate loads and which has an improved turn-off response time.

SUMMARY

Generally, the present disclosure provides new fluid heaters, methods of heating fluids and fluid heater systems. The present disclosure is operable with medical fluids, including medical fluids generally and medical fluids which must remain sterile and not directly contact the heat source. For example, the present disclosure can heat dialysis fluids, such as fluids used in hemodialysis and parenteral dialysis, and intravenous fluids. In particular, the present disclosure pertains to heating dialysate used for peritoneal dialysis, such as in continuous flow peritoneal dialysis. More specifically, the invention utilizes radiant energy from an emitter, such as energy from a radiant or infrared emitter, to heat the medical fluids as the fluids flow past the emitter.

To this end, in an embodiment of the present disclosure, a fluid heater for heating a medical fluid is provided. The heater includes a radiant heater emitting energy, wherein the energy is directed toward the fluid. A secondary heater is placed in a fluid heating position relative to the fluid. A controller operatively connects to the infrared heater and to the secondary heater, wherein the controller operates one or both of the heaters to maintain a desired temperature of the fluid.

In an embodiment, the secondary heater is a plate heater.

In an embodiment, the radiant heater includes an infrared reflector that directs the energy towards the fluid.

In an embodiment, the heater also includes at least one transmissive material disposed between the radiant heater and the fluid.

In an embodiment, the secondary heater is positioned fluidly upstream of the infrared heater.

In an embodiment, the radiant heater emits a type of energy selected from the group consisting of: infrared, microwave, laser, ultraviolet, gamma, ultrasonic, radio frequency, inductive energy and combinations thereof.

In another embodiment of the present disclosure, a device for in-line heating of fluids flowing through a disposable dialysis unit is provided. The device includes an infrared heater. The infrared heater has an infrared emitter positioned in a housing. The housing defines an opening that faces the disposable unit when the infrared heater is in use. The infrared heater has an infrared transmissive material that covers the opening. The infrared heater has an infrared reflector positioned relative to the infrared emitter such that infrared energy from the infrared emitter is substantially directed toward the infrared transmissive material.

In an embodiment, the device includes a plate heater adjacent the disposable unit.

In an embodiment, the plate heater is positioned on an opposing side of the disposable unit from the infrared heater.

In an embodiment, the device includes an infrared absorption material positioned on an opposing side of the infrared transmissive material from the infrared heater. The infrared absorption material increases in temperature from absorbing the infrared energy and heats the fluid in the disposable unit.

In an embodiment, the device includes an infrared reflective material positioned on an opposing side of the transmissive material from the infrared heater. The infrared reflective material directs at least a portion of the infrared energy outside of the housing toward the fluid in the disposable unit.

In a further embodiment of the present disclosure, a device for in-line heating of fluid flowing through a disposable unit for dialysis treatment to a patient is provided. The device includes an infrared emitter. The infrared emitter has an infrared emission in a direction toward the disposable unit when the infrared emitter is in use. A plate heater is positioned adjacent the disposable unit. A controller operatively connects to the infrared emitter and the plate heater. The controller operates one or both of the infrared emitter and the plate heater to achieve a desired fluid temperature.

In a yet another embodiment of the present disclosure, a fluid heating device for in-line heating of fluids flowing through a disposable cassette having at least one flexible membrane is provided. The device includes an infrared emitter having an infrared emission in a first direction. An infrared transmissive material is disposed between the infrared emitter and adjacent the at least one flexible membrane of the cassette. A plate heater is also positioned adjacent to the at least one flexible membrane of the cassette.

In an embodiment, the infrared transmissive material and the plate heater are adjacent the same flexible membrane on one side of the cassette.

In an embodiment, the infrared transmissive material and the plate heater are adjacent different flexible membranes on opposite sides of the cassette.

In an embodiment, the transmissive material is selected from the group consisting of: sapphire glass, optical glass, infrared glass, glass ceramics, borosilicates, aluminosilicates, fused silica (quartz), zinc sulphide, silicon, germanium, fluoride/bromide/chloride compounds and combinations thereof.

In yet a further embodiment of the present disclosure, a dialysis fluid heater for heating fluid in a fluid container is provided. The heater includes a radiant energy heater. The radiant energy heater has a radiant energy generator and a first fluid container interface. The radiant energy generator has a radiant energy emission in a direction toward the first fluid container interface. A second heater having a heat generator and a second fluid container interface is provided. The heat generator has a heat transfer emission towards the second fluid container interface. The dialysis fluid is heated by the radiant energy generator and the heat generator when the dialysis fluid is moving through the container.

In an embodiment, the radiant energy heater can heat the dialysis fluid to about 37° C.

In an embodiment, the dialysis fluid traveling at least at about 125 ml/min can be heated from about 5° C. to about 37° C.

In an embodiment, the second fluid container interface has a higher melting temperature than a temperature of the second heater.

In an embodiment, the first fluid container interface abuts a passage way in the container having a different volume than a passage abutting the second fluid container interface.

In an embodiment, the second fluid container interface abuts a baffled pathway in the container for the dialysis fluid.

Moreover, in another embodiment, a dialysis fluid heater for heating dialysis fluid in a fluid container is provided. The heater includes a first heater and a second heater cooperating with the first heater to heat the dialysis fluid. A patient can receive 2 liters of the dialysis fluid heated from about 10° C. in about 13 minutes.

In an embodiment, the first and second heaters can achieve a desired fluid temperature within about plus/minus 0.5° C.

Further still, in another embodiment, a dialysis system is provided. The system includes a fluid flow path. A radiant heater heats dialysis fluid traveling along the fluid flow path. A second heater cooperatively heats the dialysis fluid with the radiant heater along the fluid flow path.

In an embodiment, the system includes a controller that selectively energizes at least one of the radiant and second heaters to achieve a desired temperature for the dialysis fluid.

In an embodiment, the radiant and second heaters are placed in a device that additionally acts to transfer the dialysis fluid along the fluid flow path.

In still another embodiment of the present disclosure, an in-line fluid heating system for use in a dialysis system having a disposable fluid flow container is provided. The system includes a controller. A first radiant energy heater operatively connects to the controller. The first radiant energy heater has a radiant energy emission towards the disposable fluid flow container in the dialysis system when operated by the controller. A second heater operatively connects to the controller. The second heater has a heat energy emission towards the disposable fluid flow container in the dialysis system when operated by the controller. A temperature sensor couples to the controller and has a signal indicative of a sensed temperature of a dialysis fluid.

In an embodiment, the fluid flow connector fluidly connects with at least one valve.

In an embodiment, the controller receives inputs from a plurality of temperature sensors that sense dialysis fluid temperatures.

In an embodiment, the first fluid flow container includes at least one temperature sensor that senses a dialysis fluid temperature.

In an embodiment, the fluid flow container fluidly connects to at least one pump.

In an embodiment, the fluid flow container fluidly connects to a dialysis fluid storage device.

In an embodiment, the fluid flow container fluidly connects to a catheter disposed within a dialysis patient.

In still a further embodiment of the present disclosure, a method of heating dialysis fluid is provided. The method includes flowing the dialysis fluid through a disposable fluid conduit. Energy is applied from a 2-dimensional heat energy source to the dialysis fluid in the disposable fluid conduit. Energy is applied from a 3-dimensional heat energy source to the dialysis fluid in the disposable fluid conduit.

In an embodiment, applying energy from the 3-dimensional heat energy source includes employing at least one device that reflects or absorbs the 3-dimensional heat.

In an embodiment, applying energy from the 3-dimensional heat energy source includes cooling the 3-dimensional heat source.

In an embodiment, the method also includes controlling operation of the 3-dimensional heat energy source and the 2-dimensional heat energy source with a controller such that a selected one or both of the 3-dimensional and 2-dimensional heat energy sources heat the dialysis fluid.

In an embodiment, flowing the dialysis fluid includes flowing the dialysis fluid past the 2-dimensional heat energy source and subsequently flowing the dialysis fluid past the 3-dimensional heat energy source.

Still further, in an embodiment of the present disclosure, a method of in-line heating of dialysis fluid is provided. The method includes flowing the dialysis fluid through a disposable fluid conduit. The dialysis fluid is heated with a plate heater as the dialysis fluid flows past the plate heater. The dialysis fluid is heated with an infrared heater as the dialysis fluid flows past the infrared heater.

In an embodiment, flowing the dialysis fluid includes continuously flowing the dialysis fluid.

In an embodiment, the steps of heating the dialysis fluid with an infrared heater and heating the dialysis fluid with a plate heater include heating a same portion of the dialysis fluid.

In yet another embodiment of the present disclosure, a method of providing dialysis to a patient is provided. The method includes heating a dialysis fluid with a radiant heater and a second heater and passing the heated fluid into a portion of a patient.

In an embodiment, the portion includes a peritoneal cavity of the patient.

In an embodiment, the method further includes recirculating the fluid from the patient and cleaning the fluid.

In an embodiment, the method further includes reheating the recirculated fluid if necessary with at least one of the radiant heater and a second heater.

In an embodiment, the method further includes infusing the heated fluid into a sleeping patient.

In an embodiment, the method further includes infusing the heated fluid into the patient at nighttime.

In an embodiment, the method further includes heating the fluid while the patient is sleeping.

It is therefore an advantage of the present disclosure to provide improved systems for performing dialysis.

Another advantage of the present disclosure is to provide improved methods of performing dialysis.

Yet another advantage is to provide improved fluid heaters.

Another advantage of the present disclosure is to provide improved methods of heating medical fluids.

Moreover, an advantage of the present disclosure is to provide an improved system and method of performing dialysis including continuos flow dialysis.

Further, an advantage of the present disclosure is to heat fluid with radiant energy, such as infrared energy.

Still another advantage of the present disclosure is to provide systems and methods of performing dialysis at nighttime while the patient sleeps.

Yet another advantage of the present disclosure is to provide a fluid heater that employs a plurality of different types of heaters.

Another advantage of the present disclosure is to provide a heater that quickly cools upon being de-energized.

Still a further advantage of the present disclosure is to effectively heat a relatively large amount of fluid with a relatively small sized heater.

Another advantage of the present disclosure is to remove air from the heated fluid.

Yet a further advantage of the present disclosure is to heat fluid in a 3-dimensional manner as the fluid flows past the heater.

Yet another advantage of the present disclosure is to provide a dialysate heater that enables mating disposable cassettes to be reduced in size and cost.

Additional features and advantages of the present disclosure are described in, and will be apparent from, the following Detailed Description of the Invention and the figures.

BRIEF DESCRIPTION OF THE FIGURES

FIGS. 5A to 5C are elevation views of one embodiment of a disposable cassette operable with the heater of the present disclosure.

DETAILED DESCRIPTION

The present disclosure provides a dual in-line heater for use with medical fluids, in particular with dialysis fluids and most particularly with peritoneal dialysis including continuous flow peritoneal dialysis. In an embodiment, the present disclosure provides an infrared heater and a plate heater. The combination of the infrared heater and a plate heater provides efficient and effective heating of fluids over a wide-range of heating demands.

Either one or both of the infrared and the plate heaters can be used to supply the amount of heat required to increase the fluid temperature to a desired temperature. The infrared heater is a higher capacity heater, which can be selectively energized for high heat demands. The lower capacity plate heater is alternatively used alone when heat demands are relatively low, or used concurrently with the radiant heater to meet higher fluid heating demands.

The present disclosure provides for significantly increased control of heating fluids relative to existing heaters, particularly, bulk plate heaters. Both of the heaters in the present dual-heater invention, individually and in combination, provide for significantly increased temperature control of the fluid.

In an embodiment, the invention provides an in-line infrared heater in a continuous flow peritoneal dialysis system. The dialysis system automatically performs dialysis therapy on a patient, for example, while the patient naps or sleeps, at nighttime or at nighttime while the patient sleeps. In any case, the dialysis fluid used during the dialysis treatment must be heated to appropriate temperatures.

The infrared heater heats up and cools down quickly, which enables the heater to respond quickly to changes in fluid temperature or heating demands. Further, the radiant or infrared heater stops generating heat virtually the instant that the heater is de-energized.

In an embodiment, the output of the infrared and plate heaters can be selectively varied. For example, the output of the infrared heater can be reduced for lower heating demands. Or, the plate heater output can be raised to meet a heating demand that is not large enough to justify using the high capacity infrared heater.

The present disclosure thus provides a heater having great flexibility and efficiency for heating fluids over a wide-range of heating demands. The heater requires a relatively small amount of space and can be adapted to operate with existing peritoneal and other dialysis systems. The heater of the present disclosure employs 3-dimensional heating and has a relatively high watt-heat density. The heater avoids damaging the disposable components because the infrared radiation, for example, transmissively passes through the disposable component with minimal absorption. In short, the radiant heat tends to heat the dialysate fluid, not the fluid container.

Figure 1:
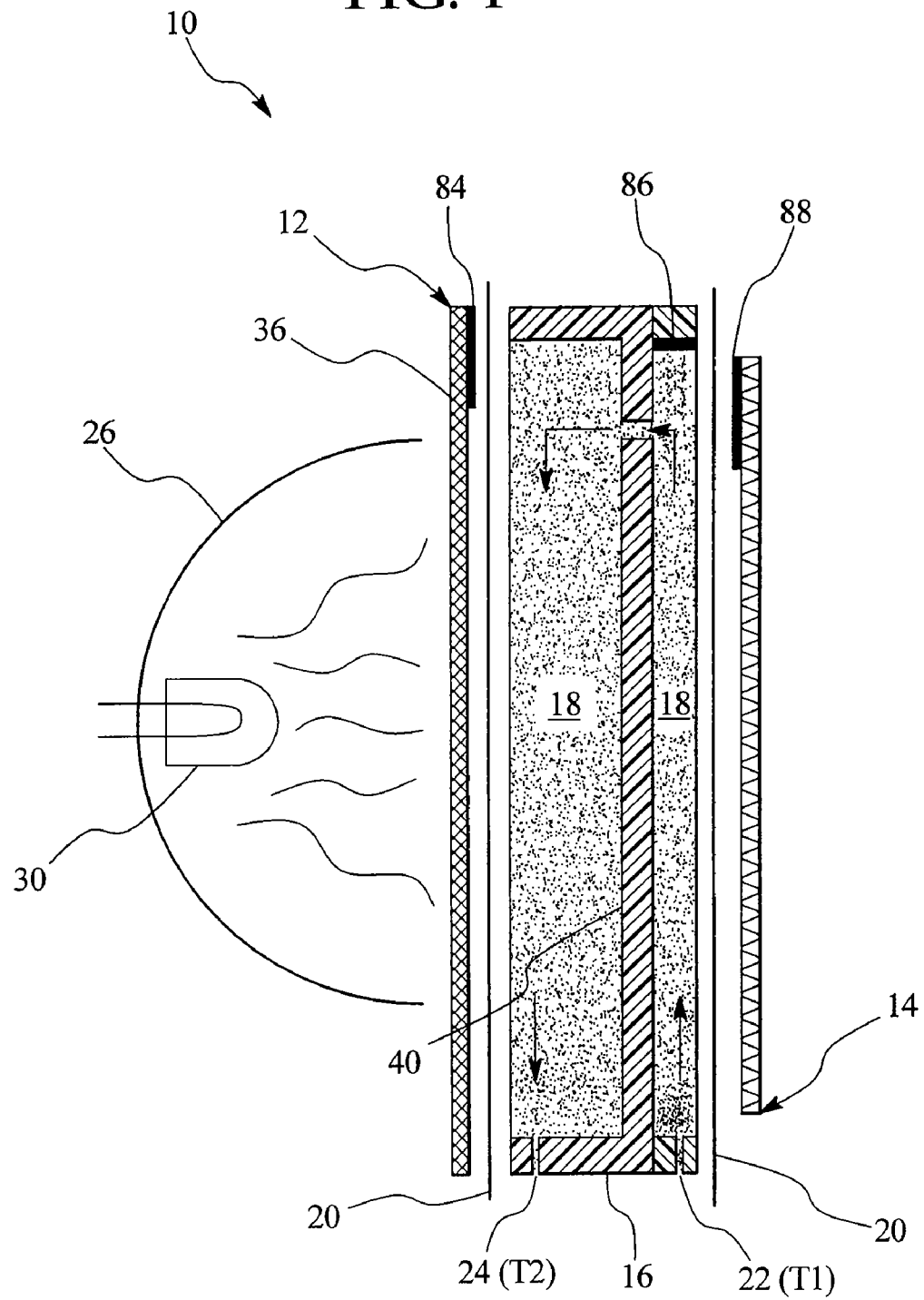
FIGS. 1 and 2 are schematic diagrams of one embodiment of the fluid heater according to the principles of the present disclosure.
Figure 2:
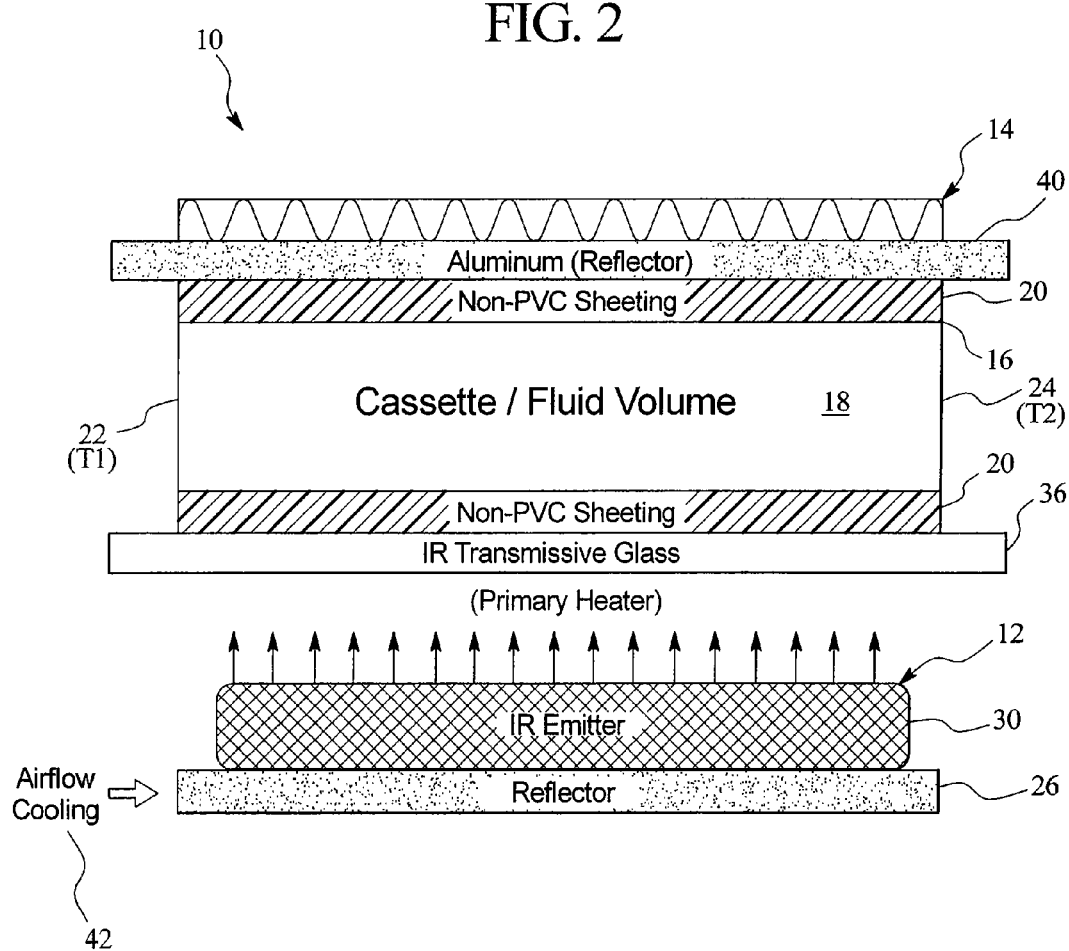

Referring now to the drawings and in particular to FIGS. 1 and 2, a heater 10 according to the invention is shown schematically. The heater 10 is a two-stage heater and has a radiant or infrared heater unit 12 and a plate heater unit 14. A fluid container 16 defining fluid flow path 18 is positioned between the infrared heater 12 and the plate heater 14. In an embodiment, the heater 10 is an in-line heater that heats fluid to desired temperatures as the fluid flows through the fluid flow path 18 past the plate and infrared heaters 14, 12. In another embodiment, however, heater 10 is sized appropriately to handle a batch operation, e.g., a bulk peritoneal dialysis transfer.

In an embodiment illustrated by FIG. 1, the path 18 is divided into an infrared portion and a plate heater portion. In an embodiment illustrated by FIG. 2, the path 18 is continuous so that both heaters 12 and 14 of the heater 10 heat the same volume of fluid at the same time. Although the infrared heater 12 and the plate heater 14 are illustrated as being on opposite sides of the container or cassette 16, in another embodiment, the heaters 12 and 14 can be positioned or reside on the same side of the cassette or container 16.

The fluid flow container 16 is in one embodiment a disposable cassette, such as the disposable cassette described in connection with FIGS. 5A to 5C. The container or disposable cassette 16 includes transmissive sides. In one embodiment, the sides are a thin, flexible sheeting 20 bonded to opposite sides of the cassette 16. The cassette sheeting 20 is generally transparent to radiant or infrared energy. For example, a polyethelene sheet of up to 8 mil thickness may be used. Other transmissive plastics may be employed.

FIG. 1 illustrates that in an embodiment, the fluid flow path 18 travels first across the plate heater 14 and then across the radiant heater 12. However, in another embodiment, the path 18 may alternatively travel past the radiant heater 12 before passing across the plate heater 14.

The infrared heater 12 uses radiant energy to heat a depth of fluid volume in a 3-dimensional manner. That is, the dialysate absorbs the radiant energy at varying depths. Dialysis fluid contains a large amount of water, and the infrared wave spectrum (from about 1.0 micron wavelength to beyond 5.0 microns wavelength) is highly absorbed by water. The infrared heater 12 also heats the internal surfaces of the disposable cassette 16, which further heats the fluid. The 3-dimensional heating of the fluid volume by the infrared heater 12 or other radiant energy emitter is a more effective and efficient heater compared with 2-dimensional plate-type heaters. Accordingly, the infrared heater 12 provides an effective heater for dialysate.

The in-line infrared heater 12 is a primary heater with a relatively high heating capacity compared to the secondary in-line plate heater 14. The infrared heater 12 is adapted to rapidly elevate the temperature of the dialysis fluid above a temperature reached by heating the dialysis fluid with the plate heater 14. For example, one heater 10 of the present disclosure includes an infrared heater 12 with a heating capacity of about three hundred to five hundred Watts and a plate heater 14 with a heating capacity of about one hundred Watts.

The plate heater 14 in an embodiment elevates the initial, cooler temperature of the dialysate. Next the radiant heater 12 heats the preheated dialysate to the desired temperature. In alternative embodiments, the radiant heater 12 elevates the initial, cooler temperature of the dialysate, and the plate heater 14 heats the preheated dialysate to the desired temperature.

It has been found that the plate heater 14 and radiant heater 12 of the heater 10 can combine to heat the dialysate traveling at about 125 ml/min from about 5° C. to about 37° C. In another example, the dual in-line heater 10 can heat fluid traveling at about 150 ml/min from about 10° C. to about 37° C. In a further example, the heater 10 can heat fluid traveling at about 200 ml/min from about 15° C. to about 37° C. Of course, the infrared and plate heaters 12, 14 can be constructed to provide any suitable combination of desired heating capacities. A patient needing 2 liters of fluid or dialysate should thus be able to receive the amount heated from about 5° C. in about 16 minutes, about 10° C. in about 13 minutes and about 15° C. in about 10 minutes. The heater 10 in an embodiment can achieve the desired fluid temperature, e.g., 37° C., within plus/minus 0.5° C.

As an in-line type heater, the heater 10 increases the temperature of the fluid as the fluid flows past the heater 10. The fluid enters a fluid inlet 22 at a temperature T1 and is heated by one or both of the plate heater 14 and the radiant or infrared heater 12 to a temperature T2 at the fluid outlet 24. The fluid heating occurs as the fluid continuously flows from the inlet 22 to the outlet 24, i.e., the fluid generally does not remain stationary within the flow path 18 while being heated. In an alternative embodiment, the heater 10 is used in a bulk fluid reservoir heating application.

Figure 3:
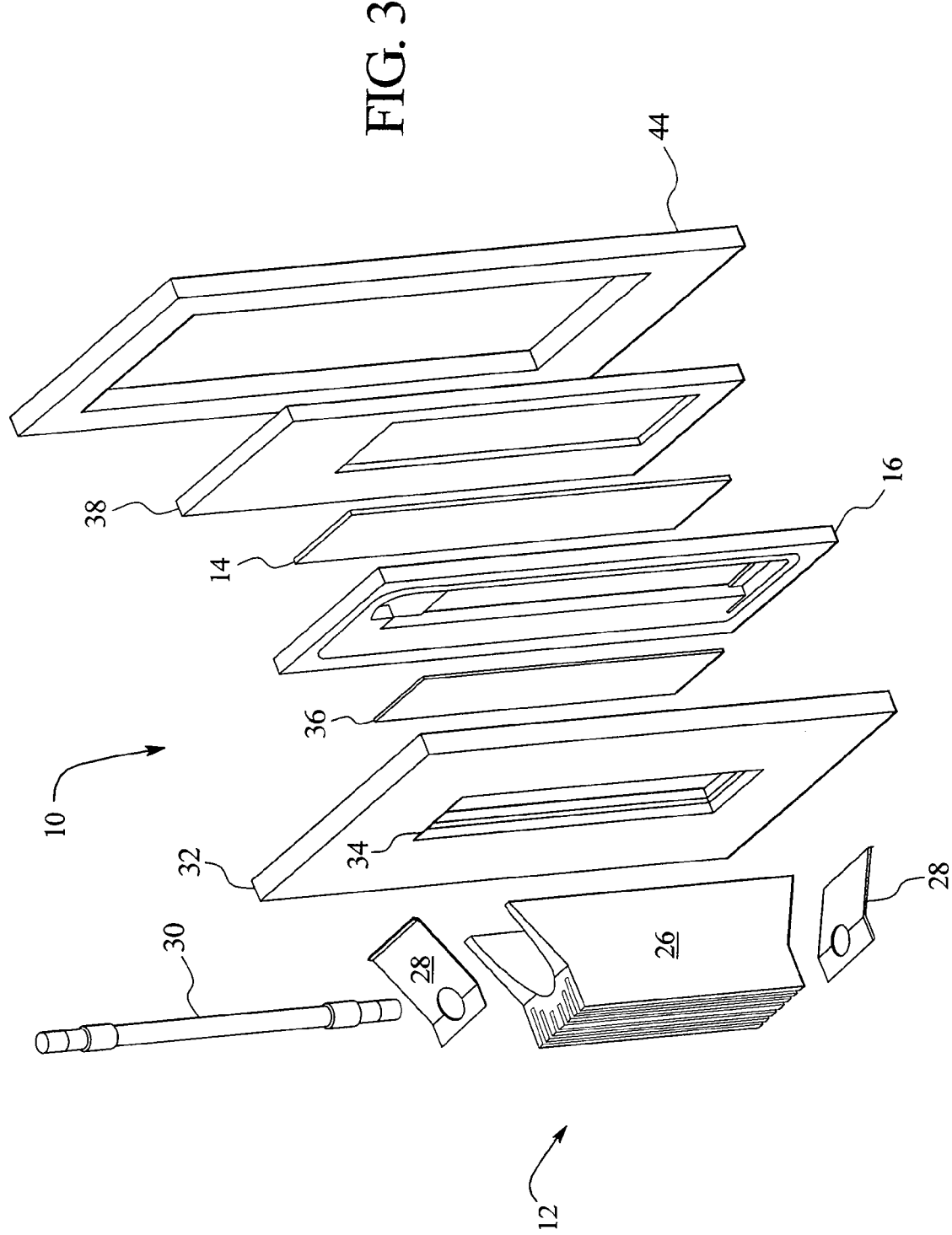
FIG. 3 is an exploded perspective view showing the assembly of one embodiment of the radiant and plate heaters of the present disclosure.

Referring now to FIGS. 1 to 3, FIG. 3 illustrates an exploded assembly of the heater 10 of the present disclosure. The heater 10 includes the separate infrared heater 12 and the plate of resistance heater 14. The infrared heater 12 includes a reflector 26. The reflector 26 is generally an elongated U-shaped or V-shaped structure, which is capped off at two ends by endcaps 28. The endcaps 28 hold a bulb 30. The bulb 30 emits radiation as described in more detail below. The reflector 26 houses the bulb 30 and channels or reflects the light from the bulb 30 towards the cassette 16. The endcaps 28 can also have a reflective surface to direct the light from the bulb 30 towards the cassette 16.

FIGS. 1 and 2 figuratively illustrate that radiant energy emits from bulb 30 and reflects off of reflector 26 towards and through a transmissive glass 36, which may or may not directly abut the transmissive plastic sheeting 20 of the cassette 16. FIG. 1 illustrates a reflector 40 that resides across the flow path 18 from the radiant heater 12, on an opposing wall of the cassette or container 20. The reflector 40, which in one embodiment is an aluminum reflecting surface, tends to capture and return the radiant energy that escapes the dialysate to increase efficiency and enhance the three dimensional heating characteristics of the system. FIG. 2 also illustrates that naturally convecting or forced air 42 may be employed to cool the radiant or infrared heater 12.

In FIG. 3, the reflector 26 of the radiant heater 12 attaches directly or indirectly to a support 32. The support 32 is a metal or plastic piece defining a cutout 34, which enables the radiant energy from the bulb 30 to pass through the support 32, through the piece of transmissive glass 36, and into the fluid traveling through the container or cassette 16 as described herein.

The resistance or plate heater 14 in an embodiment resides on or is adjacent to an opposite surface of the cassette 16, as seen in FIGS. 1 and 2. A resistance heater mount 38 holds or houses the plate heater 14. The mount 38 in an embodiment is formed of metal or molded plastic. A suitable compressive, e.g., silicone, gasket 44 enables the assembly of the heater 10 to sealingly connect or attach to the remainder of the medical or dialysis system.

The infrared heater 12 in an embodiment abuts the fluid flow container or cassette 16. The bulb 30 in an embodiment is a tungsten filament bulb or emitter. The infrared bulb or emitter 30 in an embodiment operates at a color temperature above 2000° K. and has a peak emission spectrum between one and two microns in wavelength and provides infrared energy extending beyond five microns in wavelength. When the bulb power is set to less than its rated Wattage, the filament color temperature of the bulb 30 lowers and longer wavelengths beyond 2 microns predominate.

Figure 4:
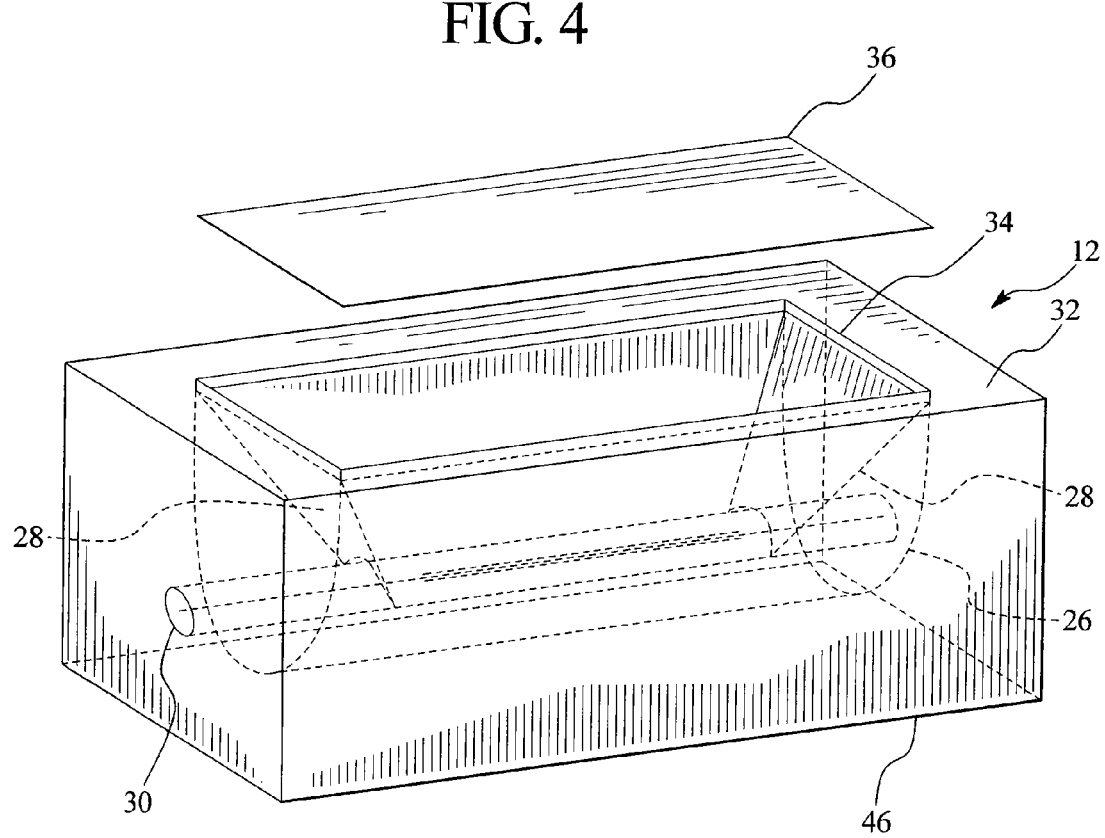
FIG. 4 is a perspective view of one embodiment of an assembly of the infrared heater according to the principles of the present disclosure.

Referring also to FIG. 4, the support 32 for the reflector 26 is integral to or attaches to a housing 46. The infrared reflector 26 resides within the housing 46. In an embodiment, the infrared reflector 26 is parabolic. The reflector 26 can alternatively have any desired shape that efficiently directs the infrared energy out of the window opening or cutout 34 defined by the support 32 of the housing 46. For example, infrared reflector 26 may alternatively be spherical, ellipsoidal or have compound curves. The reflector 26 and the endcaps 28 can have a high efficiency coating, such as a gold coating applied to a base material through a method known to those of skill in the art.

The infrared transparent glass or window 36 of the infrared heater 12 transmits most of the infrared energy from the bulb 30, so that the window 36 does not significantly increase in temperature from exposure to the infrared energy. Because the window 36 remains cool relative to the infrared bulb 30 and contacts the cassette sheeting 20, the sheeting does not experience excessive conductive heating from the glass 36, which could raise the temperature of the sheeting above its yield or melt temperatures during operation of the infrared heater 12. The window can be maintained at a temperature above the fluid temperature, and in effect, function as a plate heater and augment the infrared heating at the same interface. In an embodiment, the transmissive glass 36 is sapphire glass. In alternative embodiments, the window 36 includes optical glass, infrared glass, glass ceramics, borosilicates, aluminosilicates, fused silica (quartz), zinc sulphide, silicon, germanium, fluoride/bromide/chloride compounds as well as other types of glass.

In FIGS. 1, 2 and 3, the plate heater 14 is a resistive plate heater as is known in the art, which is capable of being placed adjacent the fluid flow container or cassette 16. In an embodiment, the plate heater 14 can also include an infrared absorption material (not illustrated) that faces the radiant heater 12. The infrared absorption material increases in temperature as it absorbs infrared energy that passes through the fluid and the various sheeting layers 20. Here, the reflective material 40 (FIG. 1) would not be used. Instead, the absorption material of the plate heater 14 absorbs the otherwise lost residual infrared energy so as to conduct more heat to the fluid and make more efficient use of the infrared energy.

In another alternative embodiment, both the infrared absorption material (not illustrated) and the infrared reflector 40 are used in combination. The infrared absorption material and the infrared reflector 40 could be placed individually or collectively at different locations on the plate heater and/or within the cassette, as desired. The infrared absorption material and/or the reflector 40 is placed in an embodiment in direct contact with the flexible sheeting 20 of the cassette.

Although the heater 10 has been mainly described as having an infrared heater 12, other radiant or 3-dimensional energy devices can be used instead of the infrared heater.

Other suitable energy sources include microwaves, ultraviolet radiation, gamma radiation, lasers, ultrasonics, radio frequencies (RF), inductive heating and others. Of course, the type of energy emitting device chosen must be compatible with the fluid that is being heated.

Referring now to FIGS. 5A, 5B and 5C, separate elevation views of one embodiment of the container or cassette 16 are illustrated. FIG. 5A shows the resistance heater side of the cassette 16. A flexible or rigid transmissive plastic sheet 20a resides as the top surface of the container 16 in FIG. 5A. The sheet 20a may be bonded to the cassette 16 and provide a sealed fluid flow path. The cassette 16 defines an inlet 22, wherein the fluid enters at an initial temperature Ti and travels to a passage 18a. As illustrated, the passage 18a includes a plurality of baffle plates 48. The baffle plates 48 mix the dialysate or medical fluid as it travels through the passage 18a, which tends to increase the heat transfer provided by the plate heater 14.

FIG. 5B illustrates the infrared heater side of the cassette 16. A flexible or rigid transmissive plastic sheet 20b resides as the top surface of the container 16 in FIG. 5B. The sheet 20b may be bonded to the cassette 16 and provide a sealed fluid flow path. The cassette defines an outlet 24, wherein the fluid exits at a final temperature T2. FIG. 5C is a sectional view of the inside of the cassette 16 taken along line 5C. As seen in FIG. 5C, the cassette 16 includes a transmissive or opaque dividing wall 50 that separates the resistance heater side of FIG. 5A from the infrared heater side of FIG. 5B. When the fluid travels from the inlet 22, through the passage 18a, the fluid passes through an opening 52 through the dividing wall 50 and into passage 18b disposed on the infrared side of the cassette 16. The passage 18b is not illustrated as having baffles 48, however, in an alternative embodiment, the passage 18b can include similarly or differently structured baffles as the baffles 48 that appear in the passage 18a.

FIG. 5C illustrates that the container 16 is generally thin and compact. The container 16 in an embodiment is disposable and is adapted to fit into the heater 10, which fits into a medical fluid flow system, such as a peritoneal dialysis system. The passage 18 (18a and 18b) and the cassette 16 may include a number of inlet ports, such as inlet 22, and a number of outlet ports, such as outlet 24. That is, the fluid may come from and exit to one or more different places depending upon the flow logic of the system.

In the embodiment illustrated in FIG. 5C, the dividing wall 50 is placed closer to the plastic sheet 20a of the resistance side than to the plastic sheet 20b of the infrared side of cassette 16. In other words, the depth of the fluid is greater in passage 18b than passage 18a. The disparity of volumes defined by the uneven placement of the divider wall 50 causes the velocity of dialysate on the resistance heater side to be higher than the velocity on the infrared heater side. One or more divider walls 50 may be positioned within the container 16 to achieve any desired fluid velocities, which can be the same or different for the component heaters 12 and 14.

The cassette 16 also can provide for air or gas separation from the fluid flowing through the cassette 16. In the embodiment of the cassette shown in FIGS. 5A, 5B, and 5C, for example, the cassette 16 is arranged vertically as shown with the opening 52 arranged upward. As the fluid passes from the passage 18a through the opening 52 to the passage 18b, gas will be separated from the fluid and collect in a gas collection area 49 at the top of the opening 52. The gas in the collection area 49 can then be removed through a vent line 51, continuously or periodically, as desired. Accordingly, the cassette 16 provides for air separation and purge from the fluid.

Figure 6:
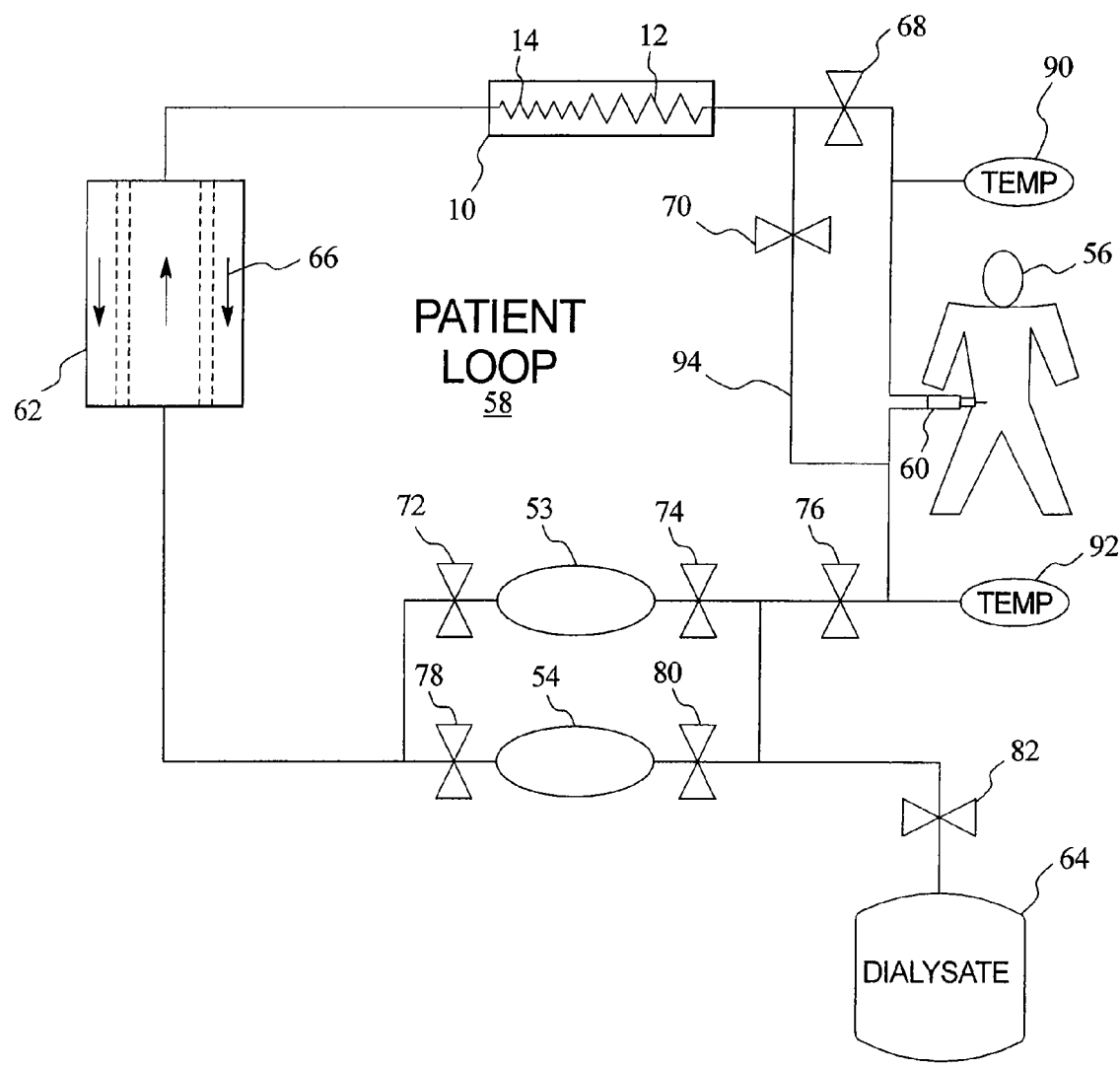
FIG. 6 is a schematic diagram of a peritoneal dialysis system having a heater according to the present disclosure.

Referring to FIG. 6, which shows a schematic diagram of a continuous flow regeneration peritoneal dialysis system, operation of the medical fluid heater of the present disclosure is illustrated. Of course, the heater 10 of the present disclosure is not meant to be limited to peritoneal dialysis treatment and may be used for any type of dialysis or medical treatment. However, peritoneal dialysis is one important use for the heater 10 of the present disclosure and its use in a peritoneal dialysis system is indicative of the use of heater 10 in other medical systems.

As illustrated, various pumps 53 and 54 continuously pump dialysis fluid into and out of a patient 56, via a patient-fluid loop 58. The patient fluid loop 58 is a continuous fluid flow path extending from a catheter 60 in the patient's peritoneal cavity, which is pumped through a dialyzer 62, through the fluid heater 10 and returning to the peritoneal cavity through the catheter 60. A regeneration fluid loop 66 extends through the dialyzer 62 and regenerates the spent dialysate in the patient fluid loop 58. Dialysate can be drawn from a dialysate source 64 as needed, such as during an initial fill of the patient's peritoneal cavity.

The flow logic is controlled by a controller (not illustrated), which can be a programmable logic controller ("PLC") or a dedicated logic controller, wherein the controller is programmed to open and close electrically or pneumatically actuated valves, e.g., valves 68 to 82. The valves can be actuated by any desired mechanism, for example, electrical, mechanical or pneumatic actuation mechanisms. Valves 68 and 70, for instance, control whether fluid flows to the patient 56 or through a by-pass line 94. Valves 72 to 80, in pairs, surround pumps 53 and 54. Valves 76 to 82 control whether the pumps 53 and 54 pump fluid to or from the patient 56 or from the dialysate source 64. FIG. 6 illustrates that before entering the patient 56, the dialysate flows through the heater 10. The fluid first flows through the plate heater 14 and then the radiant heater 12. Of course, the two heaters 12 and 14 could be reversed in order.

Demands for fluid heating can arise for many reasons. For example, dialysate from the dialysate source 64 can be stored at a temperature lower than body temperature. Here, the heater 10 is initially placed under a high demand, e.g., using the bypass line 94, to heat the bulk, cool fluid, so that the system can switch over and begin pumping fluid into the patient 56.

Heat loss can also occur during the continuous running of the dialysis system. Here, a constant but lesser demand is needed to "top-off" the system. For example, the fluid in the patient-fluid loop 58 may be exposed to ambient temperatures lower than the body temperature of the patient 56. Heat loss from the dialysate in the patient-fluid loop 58 occurs through uninsulated lines, valves and pumps. Similarly, the fluid in the regeneration fluid loop 66 of the dialyzer 62 may remove heat to the surrounding ambient environment. To correct the ambient heat loss, the fluid heater 10 heats the dialysis fluid in the patient-fluid loop 58 to desired temperatures, e.g., the human body temperature of approximately 37° C.

FIGS. 1 and 6 illustrate that the heater 10 and the system of the patient loop 58 employ a number of temperature sensors 84, 86, 88, 90, and 92. In FIG. 1, the sensor 84 monitors the temperature of the transmissive glass 36. Sensor 86 monitors the temperature of the fluid transitioning from the plate heater 14 to the infrared heater 12. Sensor 88 monitors the temperature of the plate heater 14. These sensors can sense a dangerous or melt temperature, so that the controller of the system can automatically shut down the component heaters 12 and 14.

The controller controls either one or both of the infrared heater 12 and the plate heater 14 to heat the fluid to any desired temperature. The controller (not illustrated) may turn on only the infrared heater 12 if desired, or the controller may alternatively or additionally turn on the plate heater 14. The controller may only need to run the plate heater 14, e.g., to top-off the system when it is running continuously. The controller can, of course, be programmed to use many different algorithms to run the component heaters 12 and 14 of the heater 10.

To this end, an operating temperature range for the fluid is determined and the controller automatically operates the infrared and plates heaters 12, 14 as needed to maintain the fluid temperatures within the operating range. The operator of the heater 10 may be allowed to adjust the controller to select particular fluid temperatures within the allowed temperature range. Further the controller may be adapted to have analog outputs which can vary the amount of power going to one or both the heaters 12 and 14, so that the temperature of one or both the heaters 12 and 14 can be raised or lowered. That is, the controller can control the overall temperature of the dialysate fluid by merely turning the heaters 12 and 14 on or off. Or, the controller can alternatively or additionally vary the temperature of the respective heaters 12 and 14. In an embodiment, the controller is a proportional, integral and differential ("PID") controller, which employs the three control components.

Other configurations of the heater invention are also considered within the scope of the invention. For example, the infrared heater 12 and the plate heater 14 can each have sizes, shapes, and positions to accommodate any configuration of a disposable or other fluid flow container 16. By way of example, the fluid flow container 16 could be a flexible bag, wherein the infrared heater 12 and the plate heater 14 are placed adjacent to or against the heaters. In another embodiment of the present disclosure, the infrared heater 12 is positioned adjacent to one fluid container 16 and the plate heater 14 is positioned adjacent to a second, separate fluid container 16, which fluidly connects to the first fluid container.

In an embodiment, the heater 10 includes both the infrared heater 12 and the plate heater 14. However, the plate heater 14 is omitted in an alternative embodiment, wherein only the infrared heater 12 exists to heat the fluid. As mentioned above, other radiant energy devices can be used instead of the infrared heater 12. Similarly, other heaters, such as a convection heater, may be employed instead of the resistive plate heater 14. Multiple radiant energy heaters, such as multiple infrared heaters 12, and/or multiple conduction heaters, such as the plate heater 14, could be used. These multiple radiant energy heaters and multiple conduction heaters can be constructed to have any desired heating capacity.

Furthermore, the invention can be used with fluid flow paths other than the fluid flow path 18 shown in FIG. 1. For example, the fluid flow path 18 does not necessarily have to reverse directions in the cassette 16 between the infrared heater flow path and the plate heater flow path or, the path can reverse directions multiple times. Further, as illustrated in FIG. 2, the cassette wall separating the infrared heater flow path and the plate heater flow path 18 in FIG. 1 can be removed such that there is one common flow path simultaneously contacting both the infrared and plate heaters 12, 14.

It should be understood that various changes and modifications to the present embodiments described herein will be apparent to those skilled in the art. Such changes and modifications can be made without departing from the spirit and scope of the present invention and without diminishing its intended advantages. It is therefore intended that such changes and modifications be covered by the appended Claims.

The invention claimed as follows:

1. A method of structuring a machine to heat a dialysis fluid comprising:
   supporting a radiant energy emitter via a housing having an opening;
   covering the opening with a radiant energy transmissive material;
   disposing a radiant energy reflector opposite the radiant energy emitter such that a disposable dialysis fluid pumping unit when installed is positioned between the radiant energy emitter and the radiant energy reflector;
   supporting a resistance heater so that it is adjacent to the disposable dialysis fluid pumping unit when installed; and
   wherein the radiant energy emitter, the radiant energy reflector and the resistance heater are supported and disposed such that when the disposable dialysis fluid pumping unit is installed, (i) radiant energy from the radiant energy emitter is directed towards the radiant energy transmissive material to heat the dialysis fluid within the disposable unit to a first temperature, and (ii) heating energy from the resistance heater is directed towards the disposable unit to heat the dialysis fluid to a second temperature.

2. The method of claim 1, the disposable dialysis fluid pumping unit having at least one flexible membrane, and which includes supporting the radiant energy emitter and reflector such that radiant energy can pass through the flexible membrane.

3. The method of claim 1, wherein the radiant energy emitter is an infrared emitter.

4. The method of claim 1, wherein the resistance heater is a plate heater.

5. A method of structuring a machine to heat a dialysis fluid comprising:
   supporting a radiant energy emitter via a housing having an opening;
   covering the opening with a radiant energy transmissive material;
   disposing a radiant energy reflector opposite the radiant energy emitter such that a disposable dialysis fluid pumping unit when installed is positioned between the radiant energy emitter and the radiant energy reflector;
   supporting a resistance heater so that it is adjacent to the disposable dialysis fluid pumping unit, when installed; and
   wherein the radiant energy emitter, the radiant energy reflector and the resistance heater are supported and disposed such that when the disposable dialysis fluid pumping unit is installed, (i) heating energy from the resistance heater is directed towards the disposable unit to heat the dialysis fluid within the disposable unit to a first temperature, and (ii) radiant energy from the radiant energy emitter is directed towards the radiant energy transmissive material to heat the dialysis fluid to a second temperature.

6. The method of claim 5, the disposable dialysis pumping unit having at least one flexible membrane, and which includes supporting the radiant energy emitter and reflector such that radiant energy can pass through the flexible membrane.

7. The method of claim 5, wherein the radiant energy emitter is an infrared emitter.

8. The method of claim 5, wherein the resistance heater is a plate heater.

* * * * *